United States Patent [19]
Canel et al.

[11] Patent Number: 6,143,304
[45] Date of Patent: Nov. 7, 2000

[54] ENHANCED YIELD OF PODOPHYLLOTOXIN FROM NATURAL PRODUCTS THROUGH IN SITU CONVERSION METHODS

[75] Inventors: Camilo Canel, Oxford; Franck E. Dayan, Water Valley; Rita M. Moraes; Charles L. Burandt, both of Oxford, all of Miss.

[73] Assignees: The University of Mississippi, University, Miss.; The United States of America as represented by the Secretary of Agriculture, Washington, D.C.

[21] Appl. No.: 09/376,755

[22] Filed: Aug. 17, 1999

[51] Int. Cl.[7] .................................................... A61K 35/78
[52] U.S. Cl. ............................................................ 424/195.1
[58] Field of Search ................................................ 424/195.1

[56] References Cited

U.S. PATENT DOCUMENTS 4,788,216  11/1988  Leander et al. .
5,057,616  10/1991  Jennings et al. .
5,336,605   8/1994  Sakata et al. .

*Primary Examiner*—Francisco Prats
*Assistant Examiner*—Susan D. Coe
*Attorney, Agent, or Firm*—M. Howard Silverstein; John D. Fado; Joseph A. Lipovsky

[57] ABSTRACT

Enhanced recovery of podophyllotoxin from biological sources is achieved through disruption or permeabilization of the physical integrity of cells and tissues in the presence of sufficient moisture so as to allow endogenous enzymes to convert podophyllotoxin glucosides to podophyllotoxin. Extraction of the podophyllotoxin from the plant material is then achieved by use of an organic solvent. Podophyllotoxin is used as an intermediate in the production of the antitumor agent etoposide and its analogues.

5 Claims, No Drawings

ENHANCED YIELD OF PODOPHYLLOTOXIN FROM NATURAL PRODUCTS THROUGH IN SITU CONVERSION METHODS

BACKGROUND OF THE INVENTION

1. Field of the Invention

This invention relates to means for enhanced recovery of podophyllotoxin from biological sources for its pharmaceutical use or as an intermediate in the production of antineoplastic agents.

2. Description of the Prior Art

The aryltetralin lignan podophyllotoxin is used as the starting material for the semisynthesis of the antineoplastic agents etopside and teniposide. It has also been recognized as possessing antitumor and antimitotic activities of its own. Podophyllotoxin is a natural product found in Podophyllum spp. (Berberidaceae). The main commercial source of podophyllotoxin is *P. emodii* Wall. (syn. *P. hexandrum* Royale), found in alpine and sub-alpine areas of the Himalayas. *P. emodii* has been declared an endangered species as a result of overcollection of the native population. Given the increasing medicinal importance of podophyllotoxin-derived drugs, attempts have been made to develop alternative and renewable sources for this compound. This has included the domestication and in vitro culture of *P. emodii*, the evaluation of wild harvested, cultivated and in vitro propagated *P. peltatum* (a plant native to North America commonly known as mayapple), and the utilization of other aryltetralin lignan-producing species.

Commercial production of podophyllotoxin involves its purification from an ethanolic extract of the dried roots and rhizomes of *P. emodii*, which is commercially known as Podophyllum resin or podophyllin. This resin is obtained by percolation of warm ethanol through the dried plant material, followed by precipitation with a dilute acid. Known analytical methods similarly involve extraction of the dried plant material with ethanol. Through use of these methods, the podophyllotoxin content of rhizomes and roots of *P. emodii* has been measured at 4.3% of the dry weight (Jackson et al., 1984, Aryltetralin lignans from *Podophyllum hexandrum* and *Podophyllum peltatum*, Phytochemistry 23:1147–1152). Rhizomes and leaves of *P. peltatum* have been found to respectively contain up to 0.26% and 0.54% podophyllotoxin, along with varying amounts of other aryltetralin lignans and their glycosides (Bastos et al., 1996, Quantitation of aryltetralin lignans in plant parts and among different populations of *Podophyllum peltatum* by reverse phase high performance liquid chromatography, Journal of Natural Products 59:406–408). Alternate approaches to recovering podophyllotoxin have included purely synthetic approaches (Takeya et al., 1984, Biomimetic Synthesis of Podophyllum Lignans, Chem. Pharm. Bull., 32(1): 31–37) and extraction methods making use of supercritical carbon dioxide (Choi et al.,1998, Supercritical Carbon Dioxide Extraction of Podophyllotoxin from *Dysosmia pleiantha* Roots, Planta Medica 64:482–483).

While methodologies exist for synthesis or recovery of podophyllotoxin, there remains a need for the creation of new cost-effective and sustainable methods for providing a dependable long-term supply of this material.

SUMMARY OF THE INVENTION

We have now discovered that yield of podophyllotoxin from Podophyllum spp. may be dramatically increased through use of selective processing techniques that allow the in-situ conversion of podophyllotoxin glucosides. This results from the discovery of a novel and until now uncharacterized enzymatic activity that is both stable and ubiquitously present in both aerial and underground parts of Podophyllum spp., particularly *P. peltatum*, commonly known as the mayapple. Previously unachieved levels of podophyllotoxin have been obtained from leaves of *P. peltatum* making the sustainable cultivation of this plant an attractive alternative to collection of *P. emodii* from the wild. The leaves of this species primarily store podophyllotoxin in its glucosylated form, which, until this invention, was not recoverable by presently utilized methods as podophyllotoxin. It has now been found that comminution, chemical decompartmentalization or permeabilization of the plant parts in the presence of water allows substantial in-situ enzymatic conversion of podophyllotoxin glucosides to podophyllotoxin, which may then be solvent extracted. For purposes of this application, the term "substantial" in this context is herein defined as being in excess of 50% based on stoichiometry.

Therefore, it is an object of this invention to provide a means for enhanced recovery of podophyllotoxin from native plant sources.

Another object is to provide a sustainable domestic source for podophyllotoxin.

Yet another object is to provide a cost-effective source for the production of antineoplastic agents.

Other objects and advantages of the invention will become readily apparent from the ensuing description.

DETAILED DESCRIPTION OF THE INVENTION

The present invention is based on the previously unrecognized discovery that leaves of *Podophyllum peltatum* store large quantities of podophyllotoxin primarily in the form of glucosides, which can be recovered as podophyllotoxin by bringing about their co-localization with endogenous glucosidases. In situ conversion of the glucosides to free podophyllotoxin may be accomplished through comminution, decompartmentalization, permeabilization or disruption of plant tissues in the presence of sufficient water so that the plants natural glucosidases are brought into reactive contact and allowed to effect conversion of podophyllotoxin glucosides to their active and readily recoverable form podophyllotoxin. The process, as envisioned by the inventors, is seen to encompass the disruption or comminution of plant materials at the time of harvest, when little or no additional water may need to be added to complete the endogenous conversion. Such disruption or comminution may be carried out by any available means such as grinding, sonication or chemical digestion, with the proviso that such means does not unduly reduce product yield.

In an alternate embodiment the plant materials may be partially or completely desiccated either prior or subsequent to harvest for ease of storage or transport. Subsequent disruption or comminution of the plant tissues may, at the choice of the practitioner, occur either before, during, or after any requisite rehydration. While the order of the steps of disruption/comminution and rehydration is not seen as critical, not so much time should be allowed to pass while the plant tissues are in a hydrated state so that yields of podophyllotoxin are significantly reduced due to concomitant degradative processes.

With the conditions of requisite water content and tissue disruption or permeabilization met, conversion of podophyllum glucosides to podophyllotoxin occurs. No criticality is attributed to the time or degree of grinding or comminution, which may be done when the plant material is in either the wet or dry state, with the practitioner being able to readily determine parameters yielding maximum economic advantage. Reaction conditions of time, temperature and pressure are not critical other than they not be so extreme as to cause denaturation of the glucosidase nor degradation of aryltetralin lignans or unduly inhibit the rate of reaction. With this in mind, reaction temperatures typically vary from about 10° C. to about 50° C. with reaction times ranging from about 5 seconds to about 20 minutes. While significantly longer reaction times may be utilized, such might allow degradation of the podophyllotoxin to occur, which would be undesirable from a standpoint of efficiency.

An alternate embodiment of the invention involves the use of materials such as salycilic acid, methyl jasmonate, and nitrate and vanadate ions that directly or indirectly increase membrane permeability of cellular membranes and walls such that β-glucosidase is allowed to come in reactive contact with the plants podophyllotoxin glucosides so that such may be deglycosylated to podophyllotoxin without physical disruption of the plant tissue. The thus converted podophyllotoxin may then be extracted by conventional means after grinding or comminution so as to effect efficient solvent extraction of the podophyllotoxin.

Extraction of the podophyllotoxin from the reaction mixture may be accomplished by conventional means utilizing one or more appropriate solvents; with the amounts and proportions utilized being determinable by the skilled artisan. While ethyl acetate is most preferred, other useful organic solvents include acetonitrile, acetone, n-butane, chloroform, cyclohexane, cyclopentane, dimethyl sulfoxide, ethanol, ethyl ether, hexane, heptane, isopropanol, limonene, methanol, methyl acetate, methyl ethyl ketone, n-propanol and toluene. For ease of product separation from an aqueous system, a water-immiscible solvent is desirable. Upon inclusion of the solvent in the aqueous mixture of ground or disrupted plant tissue, the resulting combination may be admixed by any conventional means such as stirring or sonication so as to enhance boundary-layer conditions and thus increase the rate and degree of podophyllotoxin recovery. The solvent is then separated from the aqueous mixture of the plant tissue and the podophyllotoxin retained therein is recovered by conventional means such as crystallization or solvent evaporation. Due to ease of separation from the hydrous plant material, a solvent lacking miscibility in water would typically be preferred.

An alternate embodiment within the scope of the instant invention includes the use of a single step to simultaneously deglycosylate and extract the podophyllotoxin from the ground or disrupted plant material. In this case the water and solvent are simultaneously made available to and admixed with the plant material. Subsequently the solvent, with its entrained podophyllotoxin, is then separated by conventional means. This approach is preferentially limited to those solvents lacking miscibility in water so as to minimize inhibitory effects by the solvent upon the endogenous deglycosylation reaction.

The following examples are intended only to further illustrate the invention and are not intended to limit the scope of the invention which is defined by the claims.

EXAMPLE 1

Plant material. Specimens of *Podophyllum peltatum* were harvested from wild accessions. Shortly after harvest, leaves and rhizomes were separated, dried at 40° C., and ground to a fine powder using a KSM 2B grinder (Braun, Lynnfield, Mass.). The powdered plant material was stored at room temperature, protected from light and moisture in tightly closed glass or plastic bottles. Dried rhizomes of *Podophyllum emodii*, originating from two localities in Northern India, were obtained from the American Mercantile Corporation (Memphis, Tenn.).

Ethanolic extraction: 40 mg of powdered tissue was mixed with 0.8 mL of 100% ethanol and incubated at ambient temperature with gentle rocking for 30 min. The mixture was clarified by centrifugation at 12,000 g for 5 min, and the supernatant transferred to a clean tube for evaporation at 45° C. using a Vacufuge Concentrator 5301 (Eppendorf). The residue was dissolved and partitioned into 0.6 mL of water and 0.6 mL of ethyl acetate. The organic phase was transferred to a new tube, evaporated, and the residue dissolved in 0.8 mL of methanol.

Aqueous extraction: 40 mg of powdered tissue was mixed with 0.6 mL of 25 mM potassium phosphate, pH 7.0, and incubated at ambient temperature with gentle rocking for 30 min. Incubation continued for another 5 min after addition of 0.6 mL of ethyl acetate. The sample was centrifuged at 12,000 g for 5 min to separate the aqueous and organic phases; the latter was collected and transferred to a new tube for evaporation. The residue was dissolved in 0.8 mL of methanol. The lignan components of this residue, including podophyllotoxin, were separated by HPLC isocratically with 28 parts of acetonitrile and 72 parts of 0.025% trifluoroacetic acid for 20 min, at a flow rate of 1 mL/min, followed by a 5-min methanol wash and re-equilibration for 15-min. The results of these protocols are shown in Table 1 below.

TABLE 1

Differential extraction of podophyllotoxin and its glucoside from powdered leaves and rhizomes of Podophyllum of various origins

| source of extract and extraction method | Yield[a] (mg/g dry wt) | |
| --- | --- | --- |
| | Podophyllotoxin-4-O-β-D-glucopyranoside | Podophyllotoxin |
| *Podophyllum peltatum* rhizomes (IN94) | | |
| ethanolic | 3.62 ± 0.23 | 3.65 ± 0.16 |
| aqueous | 0.75 ± 0.10 | 14.72 ± 0.52 |
| leaves (IN94) | | |
| ethanolic | 2.03 ± 0.10 | 4.14 ± 0.12 |
| aqueous | 0.91 ± 0.05 | 18.39 ± 0.37 |
| leaves (NC98) | | |
| ethanolic | 30.04 ± 0.91 | 10.69 ± 0.73 |
| aqueous | 0.59 ± 0.01 | 52.86 ± 3.54 |
| leaves (MO98) | | |
| ethanolic | 30.83 ± 1.55 | 10.75 ± 0.65 |
| aqueous | 0.71 ± 0.04 | 56.26 ± 2.3 |
| *Podophyllum emodii* rhizomes (HP98-1) | | |
| ethanolic | 11.8 ± 0.65 | 47.2 ± 1.14 |
| aqueous | 1.6 ± 0.05 | 53.5 ± 0.78 |
| rhizomes (HP98-2) | | |
| ethanolic | 6.4 ± 0.34 | 41.2 ± 2.08 |
| aqueous | 0.1 ± 0.02 | 39.1 ± 1.97 |

[a]Mean ± SD, n = 3.

EXAMPLE 2

One g of powdered leaves of *P. peltatum* was homogenized in 5 mL of 25 mM potassium phosphate, pH 7.0, using a hand-held glass homogenizer. The mixture was transferred to micro-centrifuge tubes and the extract clarified by centrifugation at 12,000 g for 5 min. The supernatant was collected and dialyzed against 400 mL of 25 mM potassium phosphate, pH 7.0, 10% glycerol, at 4° C. for 20 h, using dialysis cassettes of 10,000 molecular weight cutoff. The extract was mixed with one volume of glycerol and stored at −20° C.

Solutions containing 1 mg of lignan or lignan glucosides were prepared in 0.1 mL of 10 mM phosphate, pH 7. These solutions were mixed with 0.1 mL of either crude-protein extract or 50% glycerol in 10 mM phosphate, pH 7. When indicated, the protein extract was placed in a boiling-water bath for 5 min prior to mixing with the substrate. The mixtures were incubated at 37° C. for 15 min. Samples were extracted with 0.6 mL of ethyl acetate. After recovery of the organic phase and evaporation of the solvent, the residue was dissolved in 0.8 mL of methanol, of which 10 μL was analyzed by HPLC. The result of this protocol is shown in Table 2 below.

TABLE 2

In-vitro conversion of purified lignan glucosides to lignan aglycones by crude protein extracts of leaves of *Podophyllum peltatum*

| reaction components[b] | Amount of compound recovered[a] (mg) | | | |
|---|---|---|---|---|
| | 1 | 2 | 3 | 4 |
| 1 | 0.18 ± 0.08 | nd[c] | nd | nd |
| 1, protein | nd | 0.64 ± 0.08 | nd | nd |
| 1, boiled protein[d] | 0.17 ± 0.08 | nd | nd | nd |
| 3 | nd | nd | 0.79 ± 0.15 | nd |
| 3, protein | nd | nd | 0.06 ± 0.04 | 0.89 ± 0.17 |
| 3, boiled protein | nd | nd | 0.78 ± 0.11 | nd |
| 4 | nd | nd | nd | 1.04 ± 0.08 |
| 4, protein | nd | nd | nd | 0.94 ± 0.04 |
| 4, boiled protein | nd | nd | nd | 0.90 ± 0.05 |

1 α-peltatin-4-O-β-D-glucopyranoside
2 α-peltatin
3 podophyllotoxin-4-O-β-D-glucopyranoside
4 podophyllotoxin
[a]Mean ± SD, n = 3. Samples were extracted with ethyl acetate, which was then evaporated and the residue dissolved in methanol. [b]Reactions were started by mixing 0.1 mL of 10 mM potassium phosphate, pH 7, containing 1 mg of the indicated compound and 0.1 mL of either crude-protein extract or 50% glycerol in same buffer. [c]Not detected. [d]Crude-protein extract was placed in a boiling water bath for 5 min prior to use.

It is understood that the foregoing detailed description is given merely by way of illustration and that modification and variations may be made therein without departing from the spirit and scope of the invention.

We claim:

1. A method of recovering podophyllotoxin from *Podophyllum peltatum* comprising co-localizing said plant source's endogenous glucosidases and podophyllotoxin glucosides so as to bring them into reactive contact in the presence of sufficient water and effect the substantial conversion of the podophyllotoxin glucosides to podophyllotoxin, and extracting the podophyllotoxin through use of an organic solvent.

2. The method of claim 1 wherein said reactive contact is brought about by disruption or comminution of the podophyllotoxin glycoside-containing plant tissues.

3. The method of claim 1 wherein the organic solvent is selected from the group consisting of acetonitrile, acetone, n-butane, chloroform, cyclohexane, cyclopentane, dimethyl sulfoxide, ethanol, ethyl acetate, ethyl ether, hexane, heptane, isopropanol, limonene, methanol, methyl acetate, methyl ethyl ketone, n-propanol and toluene or mixtures thereof.

4. The method of claim 3 wherein the solvent is ethyl acetate.

5. The method of claim 1 wherein the reaction and extraction steps are performed simultaneously.

* * * * *